(12) United States Patent
Vanden Hoek et al.

(10) Patent No.: US 6,575,921 B2
(45) Date of Patent: Jun. 10, 2003

(54) DEVICE FOR HEART MEASUREMENT

(75) Inventors: John Vanden Hoek, Elk River, MN (US); Jody Rivers, Elk River, MN (US)

(73) Assignee: Acorn Cardiovascular, Inc., St. Paul, MN (US)

( * ) Notice: Subject to any disclaimer, the term of this patent is extended or adjusted under 35 U.S.C. 154(b) by 0 days.

(21) Appl. No.: 09/780,202

(22) Filed: Feb. 9, 2001

(65) Prior Publication Data

US 2002/0111567 A1 Aug. 15, 2002

(51) Int. Cl.$^7$ .......................... A61B 5/103; A61B 5/107
(52) U.S. Cl. .......................................... 600/587; 33/511
(58) Field of Search ............................ 600/587; 33/511, 33/512, 514.1, 555.1, 555.4, 755, 756, 759

(56) References Cited

U.S. PATENT DOCUMENTS

| | | | | |
|---|---|---|---|---|
| 2,241,451 A | * | 5/1941 | Fist | 600/591 |
| 3,983,863 A | | 10/1976 | Janke et al. | |
| 4,043,043 A | * | 8/1977 | Pace | 33/759 |

(List continued on next page.)

FOREIGN PATENT DOCUMENTS

| | | |
|---|---|---|
| DE | 33 36 121 A1 | 4/1985 |
| DE | 3831540 A1 | 4/1989 |
| DE | 3831540 C2 | 6/1993 |
| DE | 295 17 393 U1 | 3/1996 |
| EP | 0 280 564 | 8/1988 |
| GB | 2209678 | 5/1989 |
| JP | 60-203250 | 10/1985 |
| JP | 01-145066 | 6/1989 |
| RU | 986392 | 1/1983 |
| RU | 1009457 | 4/1983 |
| RU | 1232214 A1 | 5/1986 |
| WO | WO 98/29041 | 7/1998 |
| WO | WO 98/58598 | 12/1998 |
| WO | WO 99/44534 | 9/1999 |
| WO | WO 00/02500 | 1/2000 |

OTHER PUBLICATIONS

"Abstracts From the 68th Scientific Sessions, Anaheim Convention Center, Anaheim, California, Nov. 13–16, 1995", *American Heart Association Supplement to Circulation*, vol. 92, No. 8, Abstracts 1810–1813 (Oct. 15, 1995).
Capomolla et al., "Dobutamine and nitroprusside infusion in patients with severe congestive heart failure: Hemodynamic improvement by discordant effects on mitral regurgitation, left atrial function, and ventricular function", *American Heart Journal*, vol. 134, No. 6, pp. 1089–1098 (Dec. 1997).
Capouya et al., "Girdling Effect of Nonstimulated Cardiomyoplasty on Left Ventricular Function", *The Society of Thoracic Surgeons*, vol. 56, pp. 867–871 (1993).
Cohn, "The Management of Chronic Heart Failure", *The New England Journal of Medicine*, vol. 335, No. 7, pp. 490–498 (Aug. 15, 1996).

(List continued on next page.)

*Primary Examiner*—Charles A. Marmor, II
(74) *Attorney, Agent, or Firm*—Merchant & Gould P.C.

(57) ABSTRACT

A surgical tool for measuring a heart that includes a first and second handle member having proximal and distal ends and internal passageways that run lengthwise from the proximal end to the distal end, a flexible member that is cylindrically shaped with a marked proximal end that is larger in diameter than the unmarked distal end, a hinged region with a connection receiving portion on the first handle member and a connection portion on the second handle member, wherein the distal end of the flexible member passes through the internal passageway of the first handle member from the proximal end of the first handle member to the distal end of the first handle member, extends out, then enters into the distal end of the second handle member, passes through the internal passageway of the second handle member from the proximal end to the distal end of the second handle member.

14 Claims, 11 Drawing Sheets

U.S. PATENT DOCUMENTS

| | | |
|---|---|---|
| 4,048,990 A | 9/1977 | Goetz |
| 4,403,604 A | 9/1983 | Wilkinson et al. |
| 4,428,375 A | 1/1984 | Ellman |
| 4,428,385 A * | 1/1984 | Morales ..................... 600/587 |
| 4,630,597 A | 12/1986 | Kantrowitz et al. |
| 4,690,134 A | 9/1987 | Snyders |
| 4,821,723 A | 4/1989 | Baker, Jr. et al. |
| 4,834,707 A | 5/1989 | Evans |
| 4,878,890 A | 11/1989 | Bilweis |
| 4,914,821 A * | 4/1990 | Hurt .......................... 33/555.4 |
| 4,920,659 A | 5/1990 | Becher |
| 4,936,857 A | 6/1990 | Kulik |
| 4,957,477 A | 9/1990 | Lundback |
| 4,973,300 A | 11/1990 | Wright |
| 4,976,730 A | 12/1990 | Kwan-Gett |
| 5,057,117 A | 10/1991 | Atweh |
| 5,087,243 A | 2/1992 | Avitall |
| 5,131,905 A | 7/1992 | Grooters |
| 5,150,706 A | 9/1992 | Cox et al. |
| 5,184,407 A * | 2/1993 | Watrous ..................... 33/555.4 |
| 5,186,711 A | 2/1993 | Epstein |
| 5,192,314 A | 3/1993 | Daskalakis |
| 5,256,132 A | 10/1993 | Snyders |
| 5,290,217 A | 3/1994 | Campos |
| 5,356,432 A | 10/1994 | Rutkow et al. |
| 5,377,691 A | 1/1995 | Boileau et al. |
| 5,383,840 A | 1/1995 | Heilman et al. |
| 5,385,156 A | 1/1995 | Oliva |
| 5,429,584 A | 7/1995 | Chiu |
| 5,507,779 A | 4/1996 | Altman |
| 5,524,633 A | 6/1996 | Heaven et al. |
| 5,603,337 A | 2/1997 | Jarvik |
| 5,613,302 A | 3/1997 | Berman et al. |
| 5,647,380 A | 7/1997 | Campbell et al. |
| 5,702,343 A | 12/1997 | Alferness |
| 5,713,954 A | 2/1998 | Rosenberg et al. |
| 5,800,528 A | 9/1998 | Lederman et al. |
| 5,891,059 A | 4/1999 | Anderson |
| 5,920,998 A * | 7/1999 | Slilaty .......................... 33/512 |
| 6,179,791 B1 * | 1/2001 | Krueger ..................... 600/587 |

OTHER PUBLICATIONS

Coletta et al., "Prognostic value of left ventricular volume response during dobutamine stress echocardiography", *European Heart Journal*, vol. 18, pp. 1599–1605 (Oct. 1997).

Guasp, "Una protesis contentiva para el tratamiento de la miocardiopatia dilatada", *Revista Espanola de Cardiologia*, vol. 51, No. 7, pp. 521–528 (Jul 1998).

Kass et al., "Reverse Remodeling From Cardiomyoplasty in Human Heart Failure", *Circulation*, vol. 91, No. 9, pp. 2314–2318 (May 1, 1995).

Levin et al., "Reversal of Chronic Ventricular Dilation in Patients With End–Stage Cardiomyopathy by Prolonged Mechanical Unloading", *Circulation*, vol. 91, No. 11, pp. 2717–2720 (Jun. 1, 1995).

Oh et al., "The Effects of Prosthetic Cardiac Binding And Adynamic Cardiomyoplasty In A Model Of Dilated Cardiomyopathy", *The Journal of Thoracic and Cardiovascular Surgery*, vol. 116, No. 1, pp. 148–153 (Jul. 1998).

Paling, "Two–Bar Fabrics (Part–Set Threading)", *Warp Knitting Technology*, Columbine Press (Publishers) Ltd., Buxton, Great Britain, p. 111 (1970).

Vaynblat et al., "Cardiac Binding in Experimental Heart Failure", *Ann Thorac Surg*, vol. 64, (1997).

* cited by examiner

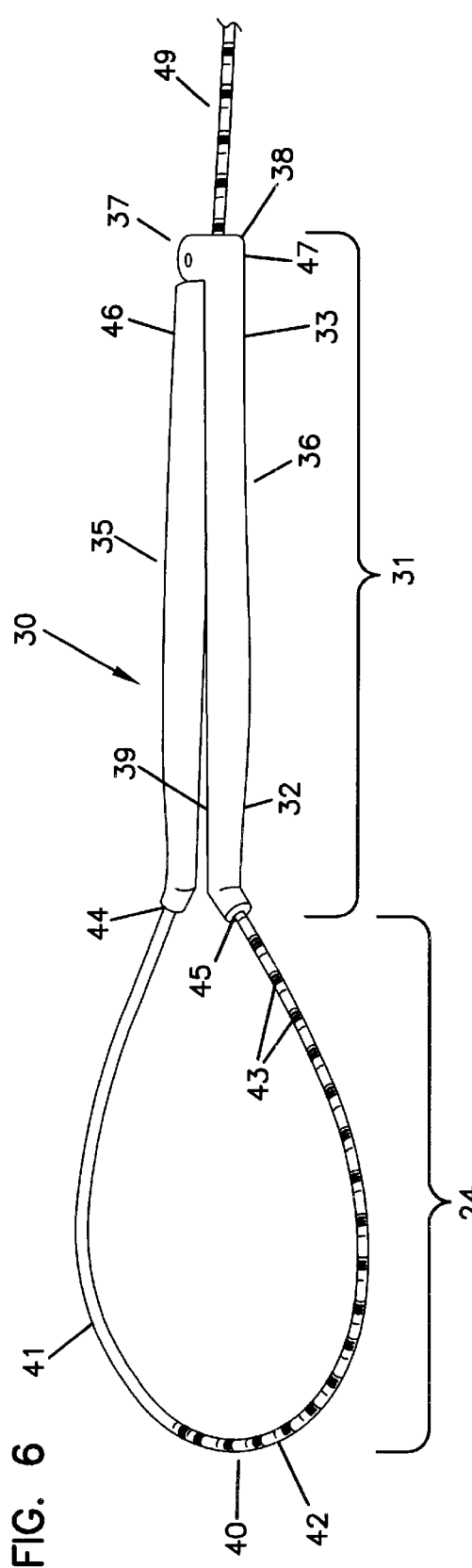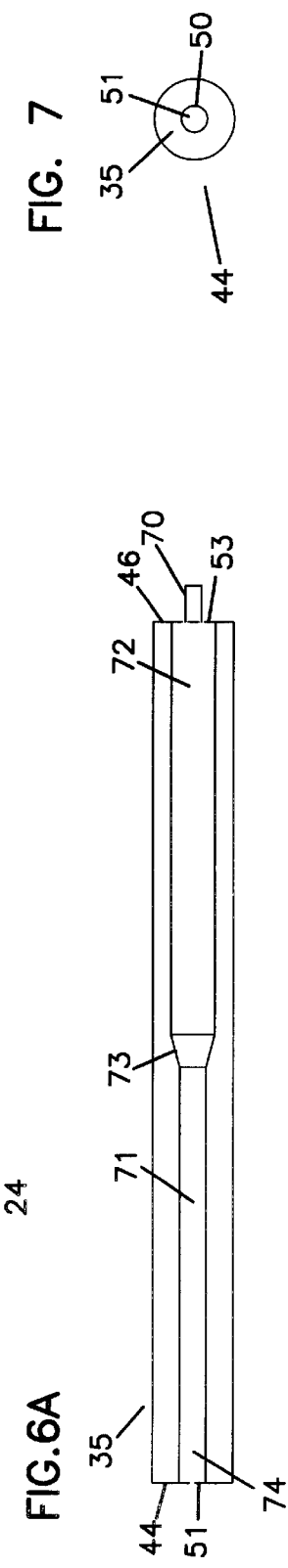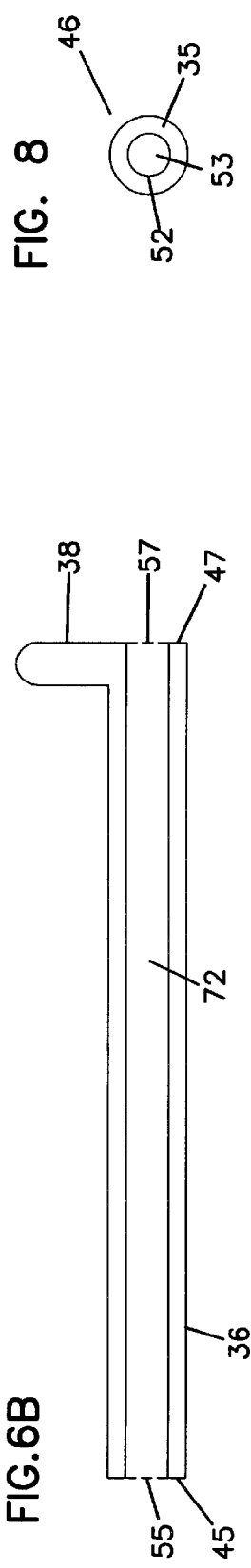

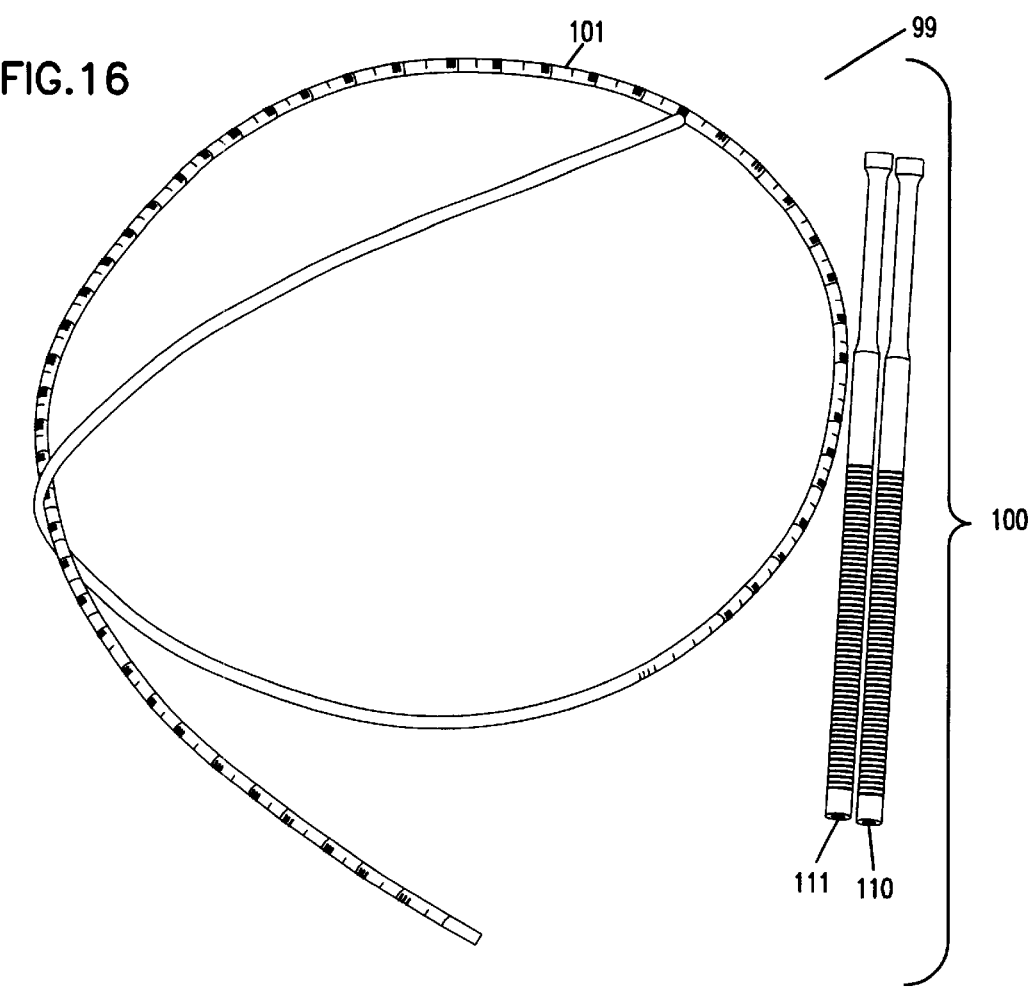
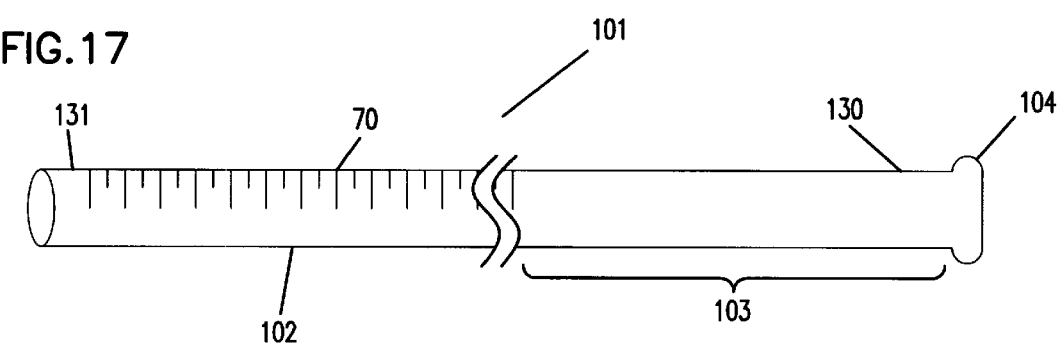
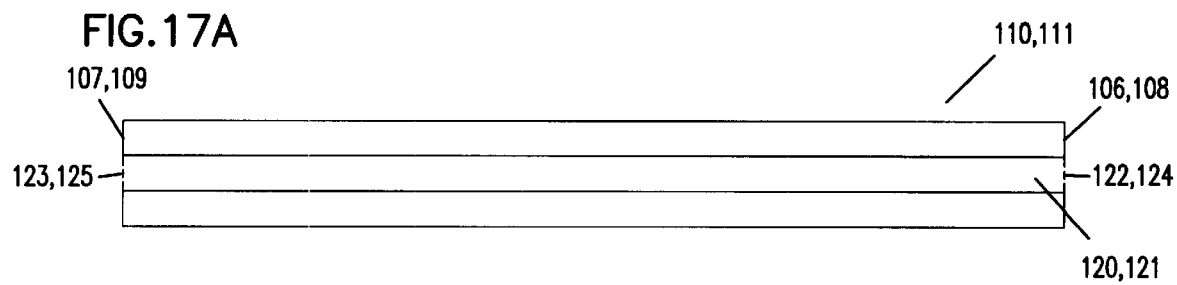

DEVICE FOR HEART MEASUREMENT

I. BACKGROUND OF THE INVENTION

1. Field of the Invention

The present invention pertains to a method and apparatus for treating congestive heart disease and related valvular dysfunction. More particularly, the present invention is directed to a measurement device for determining an appropriate size for a cardiac reinforcement device for a particular heart.

2. Description of the Prior Art

Congestive heart disease is a progressive and debilitating illness. The disease is characterized by a progressive enlargement of the heart.

As the heart enlarges, it is forced to perform an increasing amount of work in order to pump blood in each heart beat. In time, the heart becomes so enlarged the heart cannot adequately supply blood. An afflicted patient is fatigued, unable to perform even mildly exerting tasks and experiences pain and discomfort. Further, as the heart enlarges, the internal heart valves may not adequately close. This impairs the function of the valves and further reduces the heart's ability to supply blood.

Congestive heart failure has an enormous societal impact. In the United States alone, about five million people suffer from the disease (Classes I through IV combined). Alarmingly, congestive heart failure is one of the most rapidly accelerating diseases (about 400,000 new patients are diagnosed in the United States each year). Economic costs of the disease have been estimated at $38 billion annually.

Not surprisingly, substantial effort has been made to find alternative treatments for congestive heart disease. Recently, a new surgical procedure has been developed. Referred to as the Batista procedure, the surgical technique includes dissecting and removing portions of the heart in order to reduce heart volume. This is a radical, new, experimental procedure that is subject to substantial controversy. Furthermore, the procedure is highly invasive, risky and expensive and commonly includes other expensive procedures (such as a concurrent heart valve replacement).

Cardiomyoplasty is a recently developed treatment for earlier stage congestive heart disease. In this procedure, the latissimus dorsi muscle (taken from the patient's shoulder) is wrapped around the heart and chronically paced synchronously with ventricular systole. Pacing of the muscle results in muscle contraction to assist the contraction of the heart during systole.

Even though cardiomyoplasty has demonstrated symptomatic improvement, studies suggest the procedure only minimally improves cardiac performance. The procedure is highly invasive requiring harvesting a patient's muscle and an open chest approach (i.e., sternotomy) to access the heart. Furthermore, the procedure is expensive, especially when a paced muscle is utilized, because a costly pacemaker is required. The cardiomyoplasty procedure is complicated. For example, it is difficult to adequately wrap the muscle around the heart and attain a satisfactory fit. Also, if adequate blood flow is not maintained to the wrapped muscle, the muscle may necrose. The muscle may stretch after wrapping, reducing its constraining benefits, and the muscle is generally not susceptible to post-operative adjustment. Finally, the muscle may fibrose and adhere to the heart causing undesirable constraint on the contraction of the heart during systole.

While cardiomyoplasty has resulted in symptomatic improvement, the nature of the improvement is not understood. For example, one study has suggested the benefits of cardiomyoplasty are derived less from active systolic assist than from remodeling, perhaps because of an external elastic constraint. The study suggests an elastic constraint (i.e., a non-stimulated muscle wrap or an artificial elastic sock placed around the heart) could provide similar benefits. Kass et al., *Reverse Remodeling From Cardiomyoplasty In Human Heart Failure: External Constraint Versus Active Assist*, 91 *Circulation* 2314–2318 (1995). Similarly, cardiac binding is described in Oh et al., *The Effects of Prosthetic Cardiac Binding and Adynamic Cardiomyoplasty in a Model of Dilated Cardiomyopathy*, 116 *J. Thorac. Cardiovasc. Surg.* 148–153 (1998), Vaynblat et al., *Cardiac Binding in Experimental Heart Failure*, 64 *Ann. Thorac. Surg.* 81–85 (1997) and Capouya et al., *Girdling Effect of Nonstimulated Cardiomyoplasty on Left Ventricular Function*, 56 *Ann. Thorac. Surg.* 867–871 (1993).

In addition to cardiomyoplasty, mechanical assist devices have been developed as intermediate procedures for treating congestive heart disease. Such devices include left ventricular assist devices ("LVAD") and total artificial hearts ("TAH"). An LVAD includes a mechanical pump for urging blood flow from the left ventricle into the aorta. Such surgeries and devices are expensive. The devices are at risk of mechanical failure and frequently require external power supplies. TAH devices are used as temporary measures while a patient awaits a donor heart for transplant.

Commonly assigned U.S. Pat. No. 5,702,343 to Alferness dated Dec. 30, 1997 teaches a jacket to constrain cardiac expansion during diastole. Also, PCT International Publication No. WO 98/29401 published Jul. 9, 1998 teaches a cardiac constraint in the form of surfaces on opposite sides of the heart with the surfaces joined together by a cable through the heart or by an external constraint. U.S. Pat. No. 5,800,528 dated Sep. 1, 1998 teaches a passive girdle to surround a heart. German utility model DE 295 17 393 describes a non-expansible heart pouch. PCT International Publication No. WO 98/58598 published Dec. 30, 1998 describes a cardiac pouch with an elastic limit.

II. BRIEF DESCRIPTION OF THE DRAWINGS

FIG. 6 is a plan view of one embodiment of the invention.

FIGS. 6a and b are cross sectional views of handle members 35 and 36.

Figure 9:
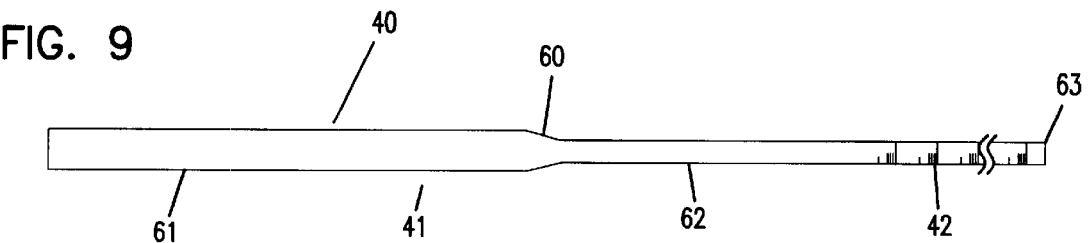
Figure 10:
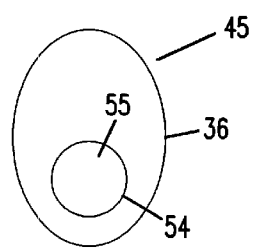
Figure 11:
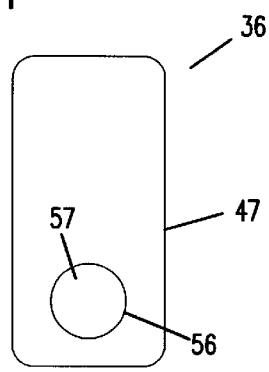
Figure 12:
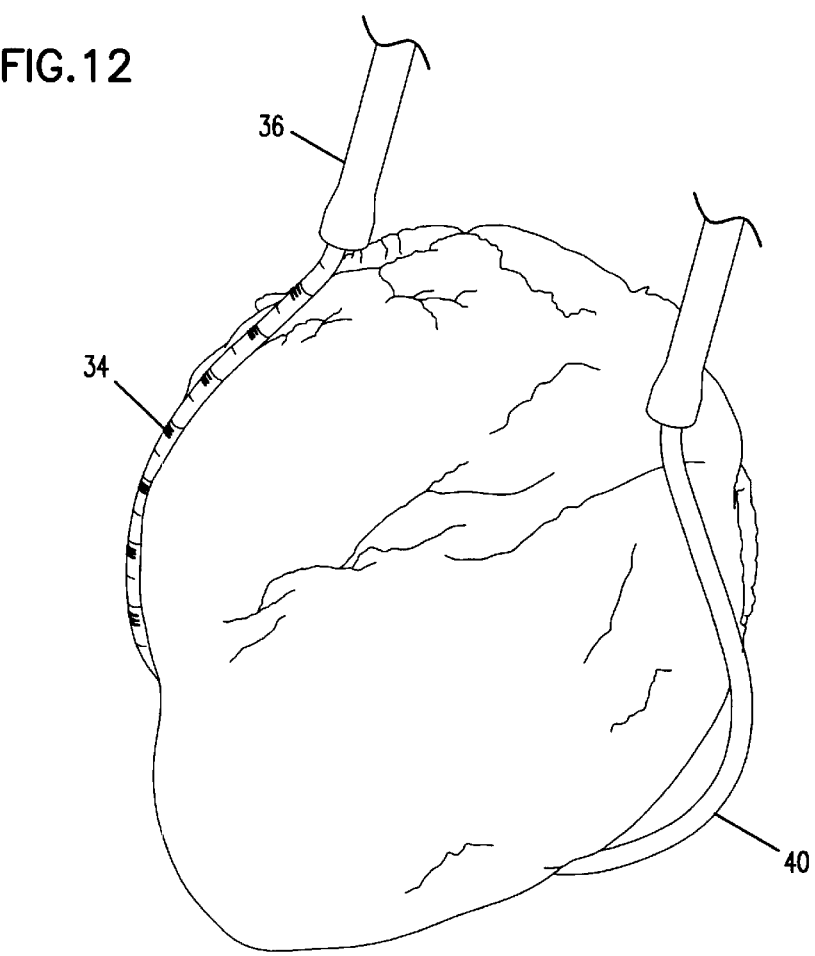
Figure 13:
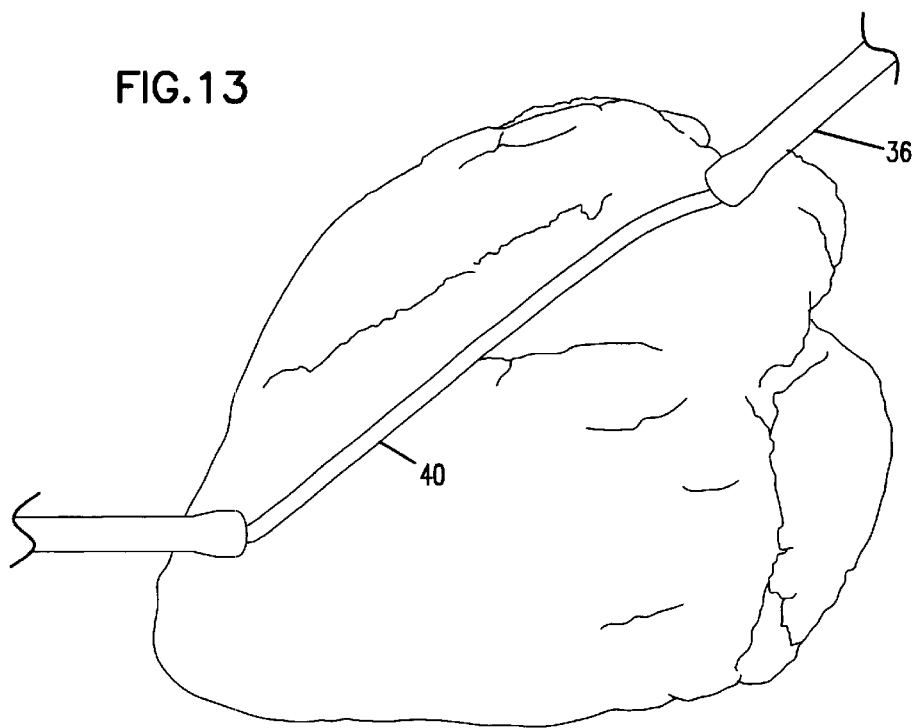
Figure 14:
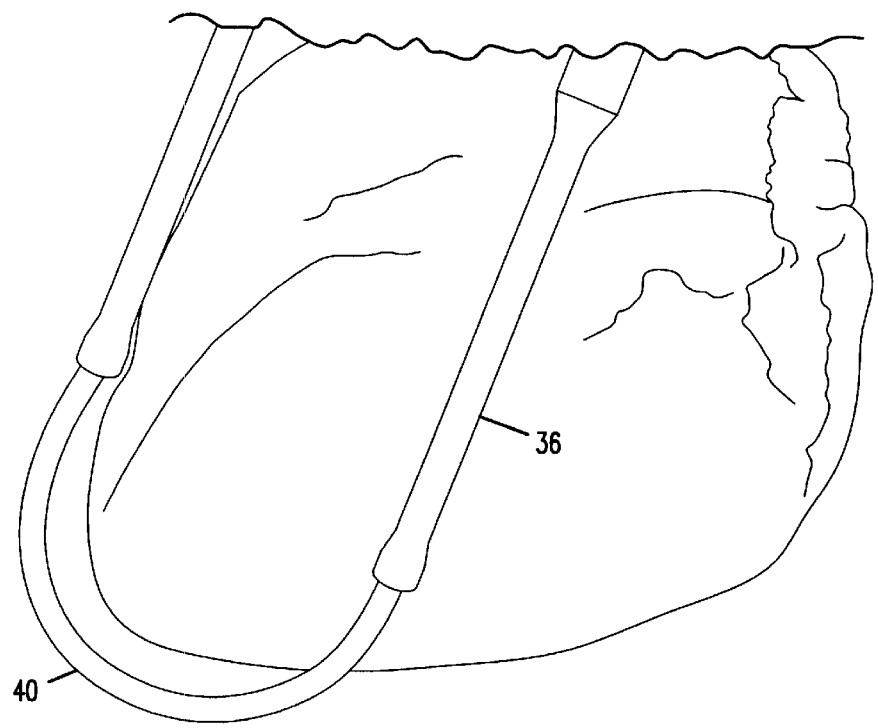
Figure 15:
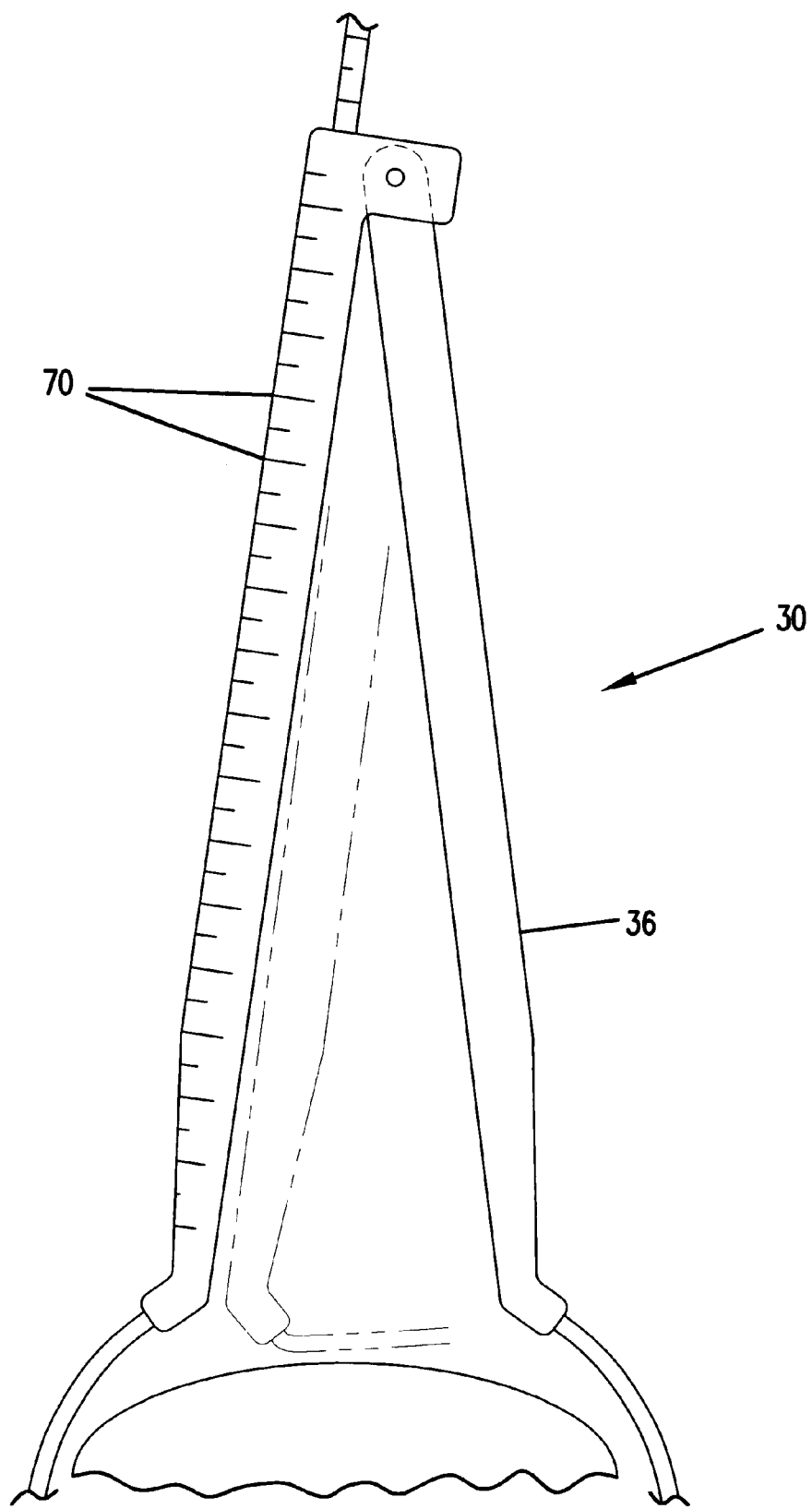
Figure 18:
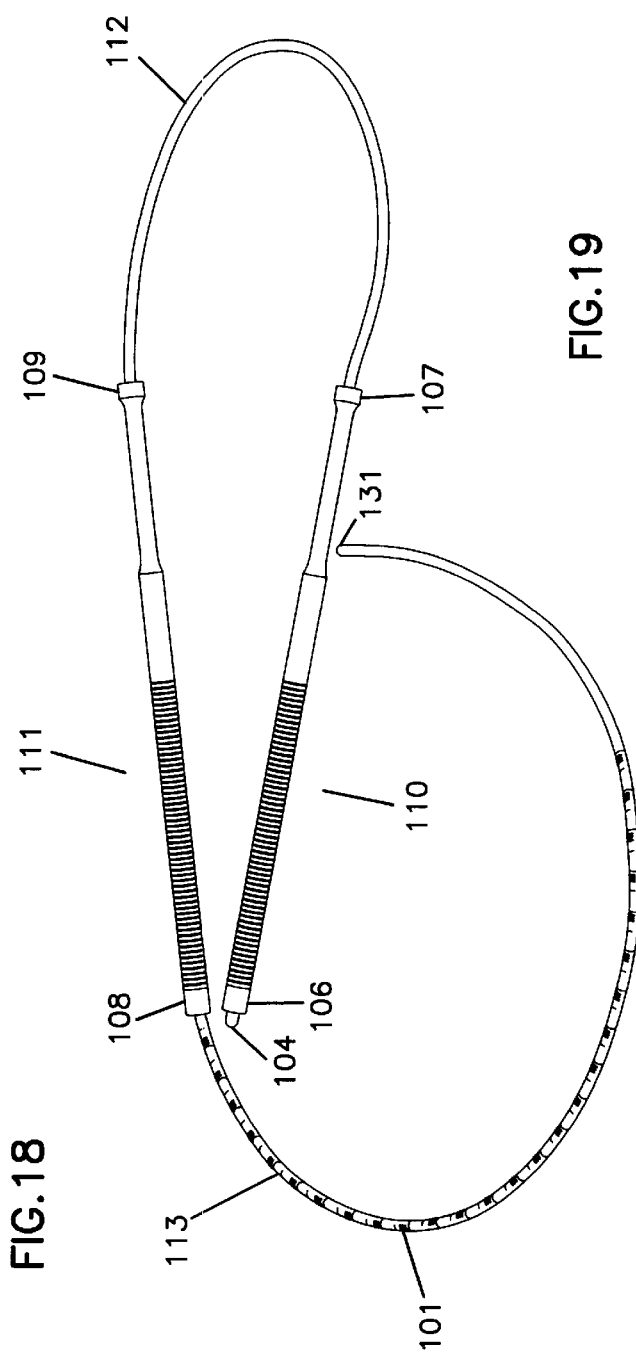
Figure 19:
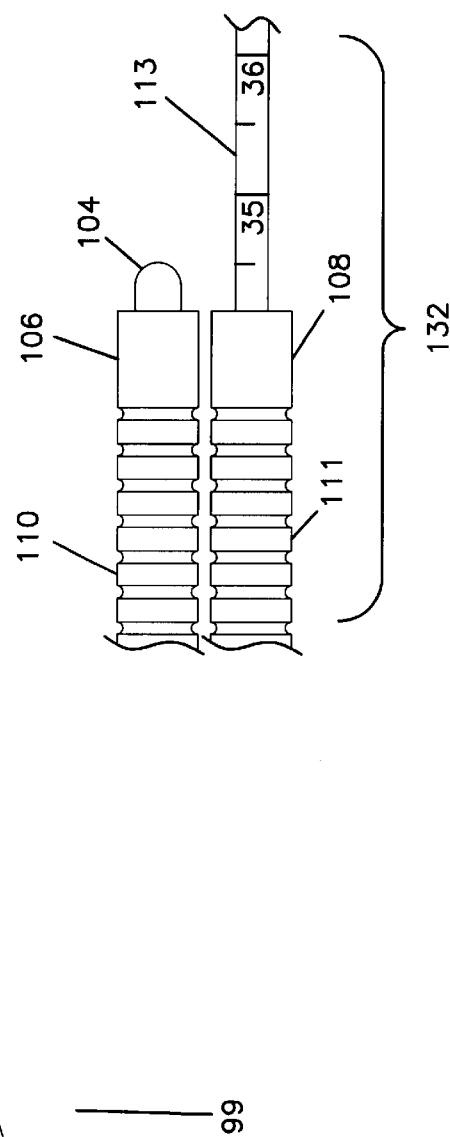

FIG. 7 is a cross sectional view of the distal end of handle member 35 of the embodiment of the invention depicted in FIG. 6;

FIG. 8 is a cross-sectional view of the proximal end of handle member 35 of the embodiment of the invention depicted in FIG. 6;

FIG. 9 is a plan view of a cylindrical tube used in the embodiment of the invention depicted in FIG. 6;

FIG. 10 is a cross-sectional view of the distal end of handle member 36 of the embodiment of the invention depicted in FIG. 6;

FIG. 11 is a cross-sectional view of the proximal end of handle member 36 of the embodiment of the invention depicted in FIG. 6;

FIG. 12 is a side elevation view depicting measurement of a size of a heart with the device of the invention;

FIG. 13 is a side elevation view depicting measurement of the surface length of the heart with the device of the invention;

FIG. 14 is a side elevation view depicting measurement of the apex of the heart with the device of the invention;

FIG. 15 is a plan view of the embodiment depicted in FIG. 6 with a handle member labeled with markings to allow for use as a ruler;

FIG. 16 is an unassembled plan view of another embodiment of the invention;

FIG. 17 is a plan view of the cylindrical flexible member used in the embodiment of the invention depicted in FIG. 16;

FIG. 17a is a cross sectional view of the cylindrical tube used with the flexible member shown in FIG. 17 which can be used as a first and second handle member of this embodiment of the invention;

FIG. 18 is an assembled plan view of the embodiment of the invention depicted in FIG. 16;

FIG. 19 is a plan view of the proximal end of the handle of the device depicted in FIG. 18.

III. DESCRIPTION OF THE PREFERRED EMBODIMENT

One method of treating congestive heart disease is by placement of a cardiac constraint device around the enlarged heart. Constraint devices are slipped onto the heart and adjusted to give the desired tension upon the heart. Tightening of the device is important because the device can neither be too tight nor too loose. In order to make tightening of the cardiac constraint device easy, measurements of the heart must be made.

Commonly assigned co-pending U.S. application Ser. No. 09/399,703, now U.S. Pat. No. 6,179,791, describes a tool that can be used for measuring the heart. In order to make such measurements, an incision must be made in the patient's chest to allow the tool to be placed around the heart. Applicant's invention provides an improvement upon the preceding surgical tool by allowing a smaller incision to accomplish such measurements.

Applicant's invention provides a device capable of measuring various parameters of a patient's heart. The tool can provide such measurements through smaller incisions in the patient. The tool of the Applicant's invention is also simple to construct, made of low cost materials to allow for single usage, and is configured for simple and efficient usage by a surgeon.

A. Congestive Heart Disease

To facilitate a better understanding of the present invention, description will first be made of a cardiac constraint device such as is more fully described in commonly assigned U.S. Pat. No. 6,085,754. In the drawings, similar elements are labeled similarly throughout.

Figure 1A:
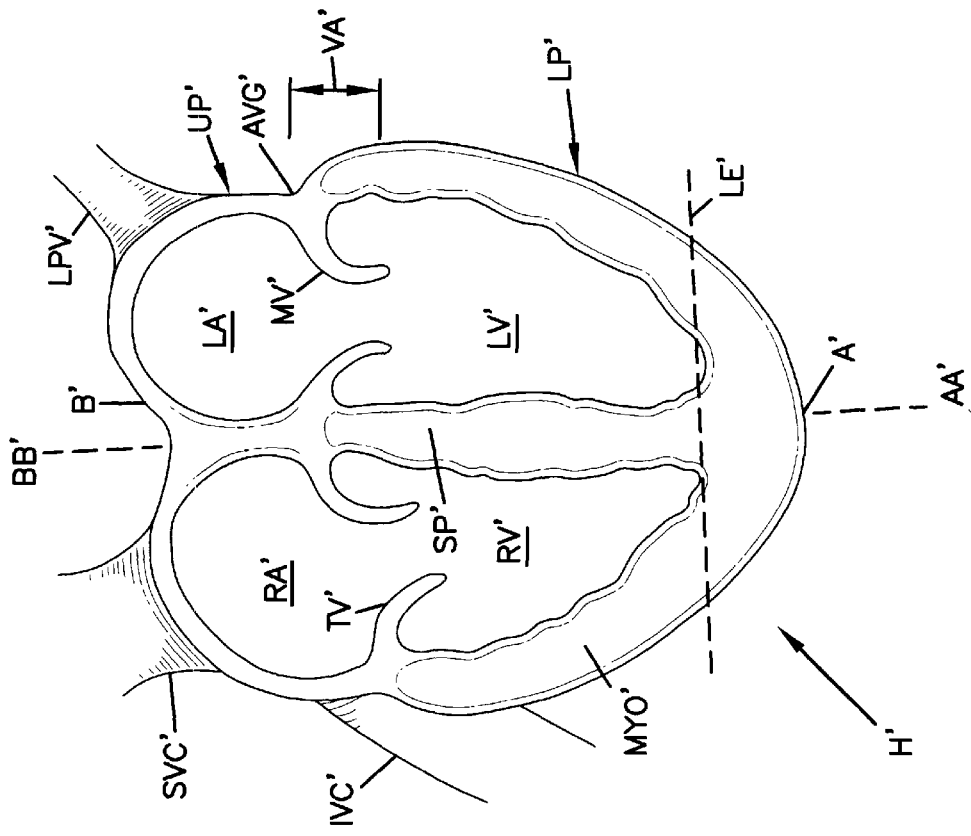
FIG. 1A is the view of FIG. 1 showing the heart during diastole.
Figure 1:
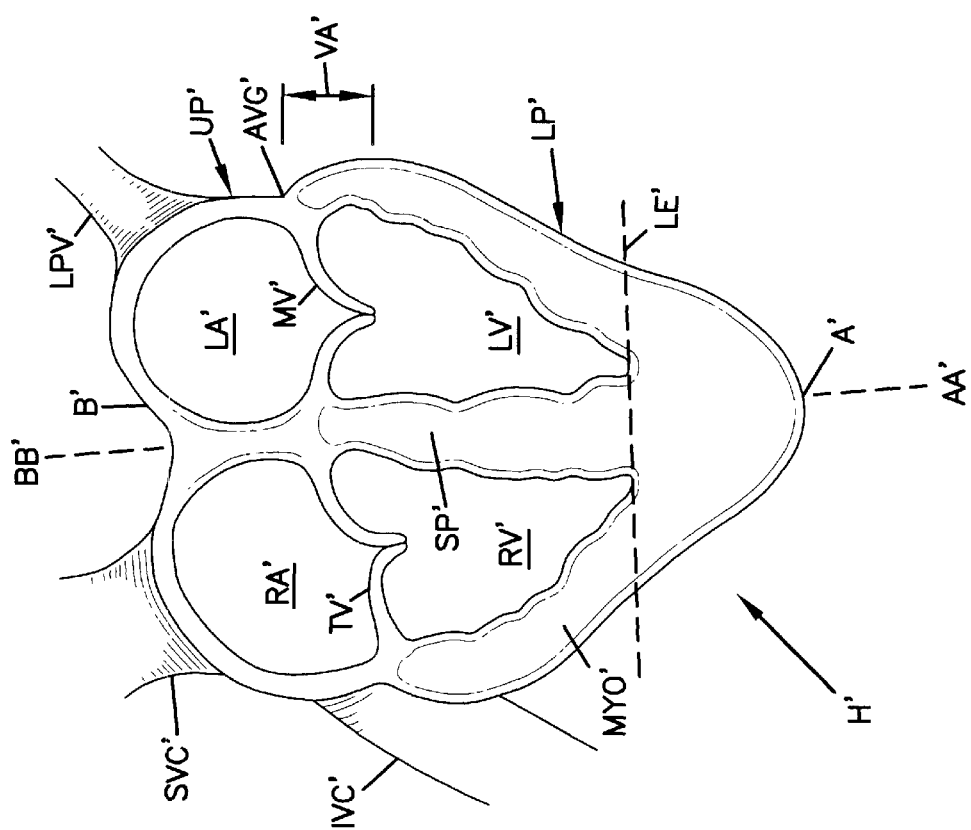
FIG. 1 is a schematic cross-sectional view of a normal, healthy human heart shown during systole.

With initial reference to FIGS. 1 and 1A, a normal, healthy human heart H' is schematically shown in cross-section and will now be described in order to facilitate an understanding of the present invention. In FIG. 1, the heart H' is shown during systole (i.e., high left ventricular pressure). In FIG. 1A, the heart H' is shown during diastole (i.e., low left ventricular pressure).

The heart H' is a muscle having an outer wall or myocardium MYO' and an internal wall or septum SP'. The myocardium MYO' and septum SP' define four internal heart chambers including a right atrium RA', a left atrium LA', a right ventricle RV' and a left ventricle LV'. The heart H' has a length measured along a longitudinal axis BB'-AA' from an upper end or base B' to a lower end or apex A'.

The right and left atria RA', LA' reside in an upper portion UP' of the heart H' adjacent the base B'. The right and left ventricles RV', LV' reside in a lower portion LP' of the heart H' adjacent the apex A'. The ventricles RV', LV' terminate at ventricular lower extremities LE' adjacent the apex A' and spaced there from by the thickness of the myocardium MYO'.

Due to the compound curves of the upper and lower portions UP', LP', the upper and lower portions UP', LP' meet at a circumferential groove commonly referred to as the A-V (atrio-ventricular) groove AVG'. Extending away from the upper portion UP' are a plurality of major blood vessels communicating with the chambers RA', RV', LA', LV'. For ease of illustration, only the superior vena cava SVC', inferior vena cava IVC' and a left pulmonary vein LPV' are shown as being representative.

The heart H' contains valves to regulate blood flow between the chambers RA', RV', LA', LV' and between the chambers and the major vessels (e.g., the superior vena cava SVC', inferior vena cava IVC' and a left pulmonary vein LPV'). For ease of illustration, not all of such valves are shown. Instead, only the tricuspid valve TV' between the right atrium RA' and right ventricle RV' and the mitral valve MV' between the left atrium LA' and left ventricle LV' are shown as being representative.

The valves are secured, in part, to the myocardium MYO' in a region of the lower portion LP' adjacent the A-V groove AVG' and referred to as the valvular annulus VA'. The valves TV' and MV' open and close through the beating cycle of the heart H.

FIGS. 1 and 1A show a normal, healthy heart H' during systole and diastole, respectively. During systole (FIG. 1), the myocardium MYO' is contracting and the heart assumes a shape including a generally conical lower portion LP'. During diastole (FIG. 1A), the heart H' is expanding and the conical shape of the lower portion LP' bulges radially outwardly (relative to axis AA'-BB').

The motion of the heart H' and the variation in the shape of the heart H' during contraction and expansion is complex. The amount of motion varies considerably throughout the heart H'. The motion includes a component which is parallel to the axis AA'-BB' (conveniently referred to as longitudinal expansion or contraction). The motion also includes a component perpendicular to the axis AA'-BB' (conveniently referred to as circumferential expansion or contraction).

Having described a healthy heart H' during systole (FIG. 1) and diastole (FIG. 1A), comparison can now be made with a heart deformed by congestive heart disease. Such a heart H is shown in systole in FIG. 2 and in diastole in FIG. 2A. All elements of diseased heart H are labeled identically with similar elements of healthy heart H' except only for the omission of the apostrophe in order to distinguish diseased heart H from healthy heart H'.

Figure 2A:
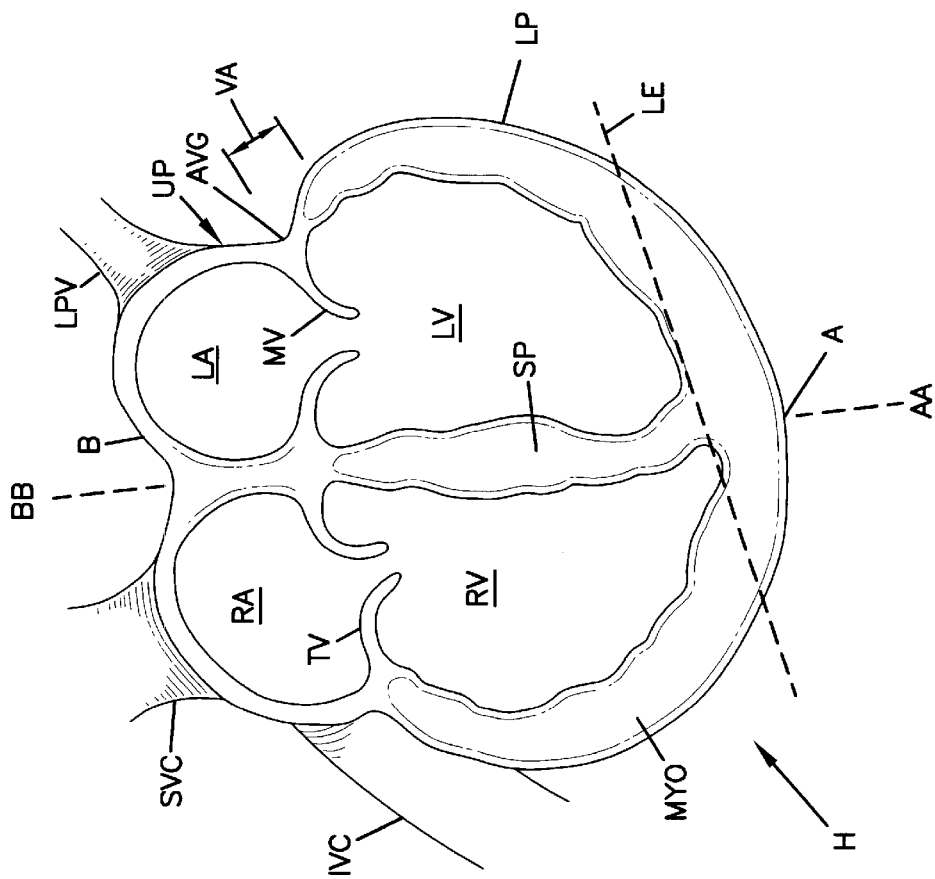
FIG. 2A is the view of FIG. 2 showing the heart during diastole.
Figure 2:
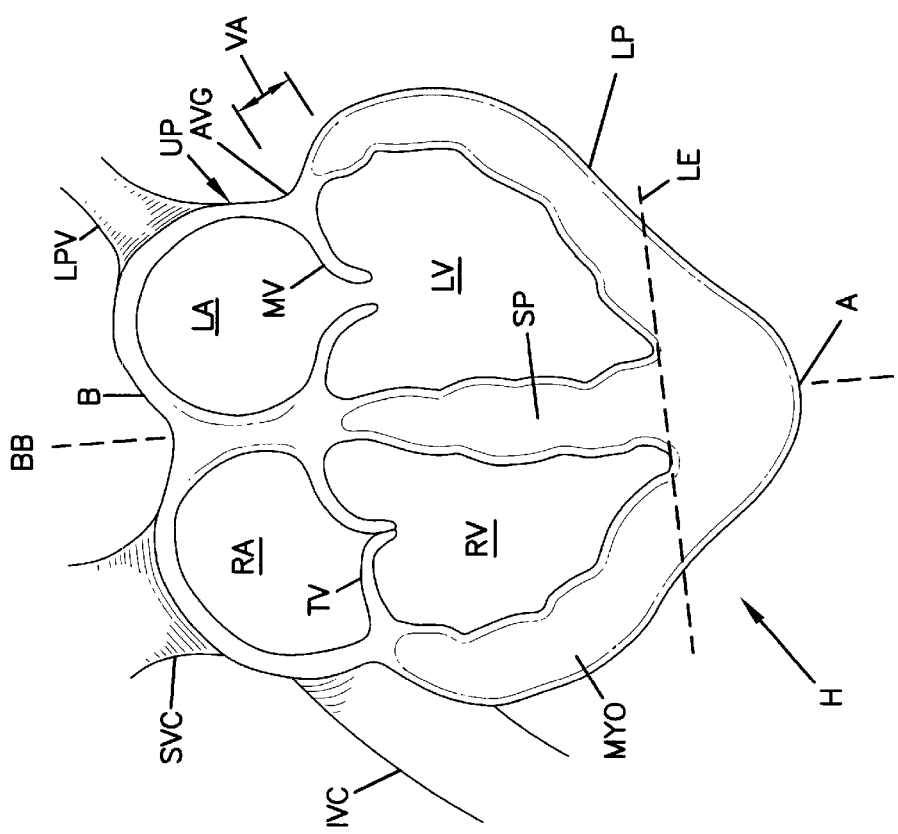
FIG. 2 is a schematic cross-sectional view of a diseased human heart shown during systole.

Comparing FIGS. 1 and 2 (showing hearts H' and H during systole), the lower portion LP of the diseased heart H has lost the tapered conical shape of the lower portion LP' of the healthy heart H'. Instead, the lower portion LP of the diseased heart H dilates outwardly between the apex A and the A-V groove AVG. So deformed, the diseased heart H during systole (FIG. 2) resembles the healthy heart H' during diastole (FIG. 1A). During diastole (FIG. 2A), the deformation is even more extreme.

As a diseased heart H enlarges from the representation of FIGS. 1 and 1A to that of FIGS. 2 and 2A, the heart H becomes a progressively more inefficient pump. Therefore, the heart H requires more energy to pump the same amount of blood. Continued progression of the disease results in the heart H being unable to supply adequate blood to the patient's body and the patient becomes symptomatic of cardiac insufficiency.

For ease of illustration, the progression of congestive heart disease has been illustrated and described with reference to a progressive dilation of the lower portion LP of the heart H. While such enlargement of the lower portion LP is most common and troublesome, enlargement of the upper portion UP may also occur.

In addition to cardiac inefficiency, the enlargement of the heart H can lead to valvular disorders. As the circumference of the valvular annulus VA increases, the leaflets of the valves TV and MV may spread apart. After a certain amount of enlargement, the spreading may be so severe that the leaflets cannot completely close. Incomplete closure results in valvular regurgitation contributing to an additional degradation in cardiac performance. While circumferential enlargement of the valvular annulus VA may contribute to valvular dysfunction as described, the separation of the valve leaflets is most commonly attributed to deformation of the geometry of the heart H.

B. Cardiac Constraint Therapy

Having described the characteristics and problems of congestive heart disease, a treatment method and apparatus are described in commonly assigned U.S. Pat. No. 6,085,754. In general, a jacket is configured to surround the myocardium MYO. While the method of the present invention will be described with reference to a jacket as described in commonly assigned U.S. Pat. No. 6,085,754, it will be appreciated that the present invention is applicable to other cardiac constraint devices including those shown in U.S. Pat. No. 5,800,528 and PCT International Publication No. WO 98/29401.

Figure 3A:
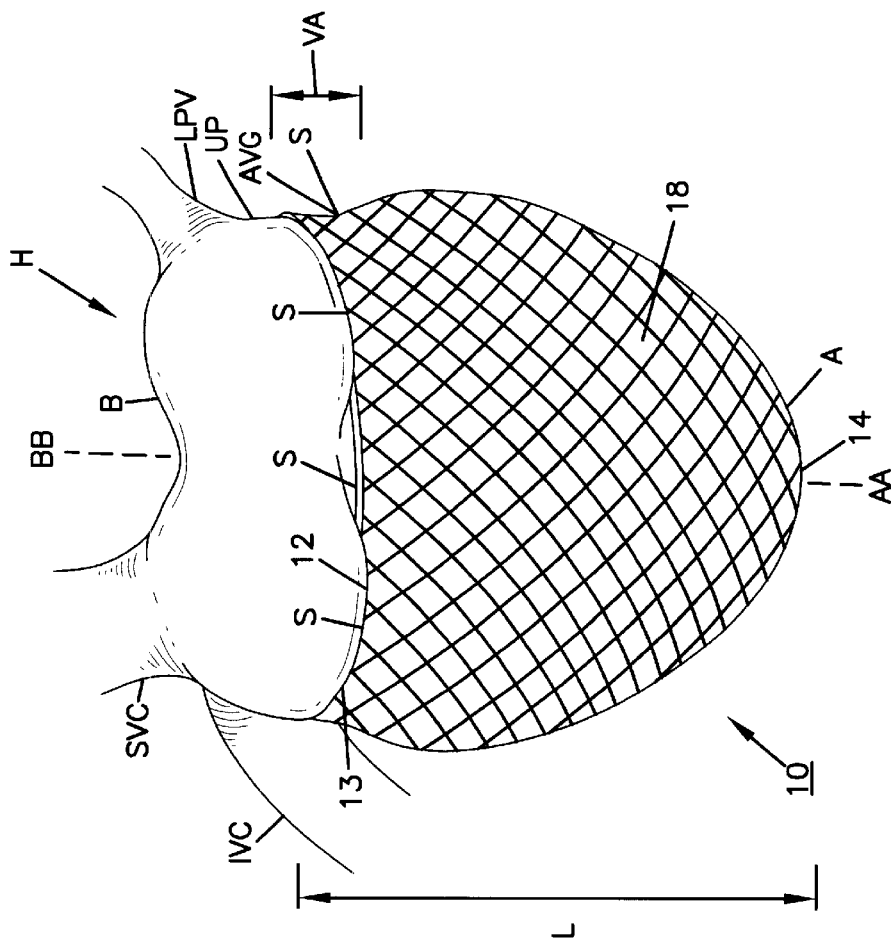
FIG. 3A is a side elevation view of a diseased heart in diastole with the device of FIG. 3 in place.
Figure 3:
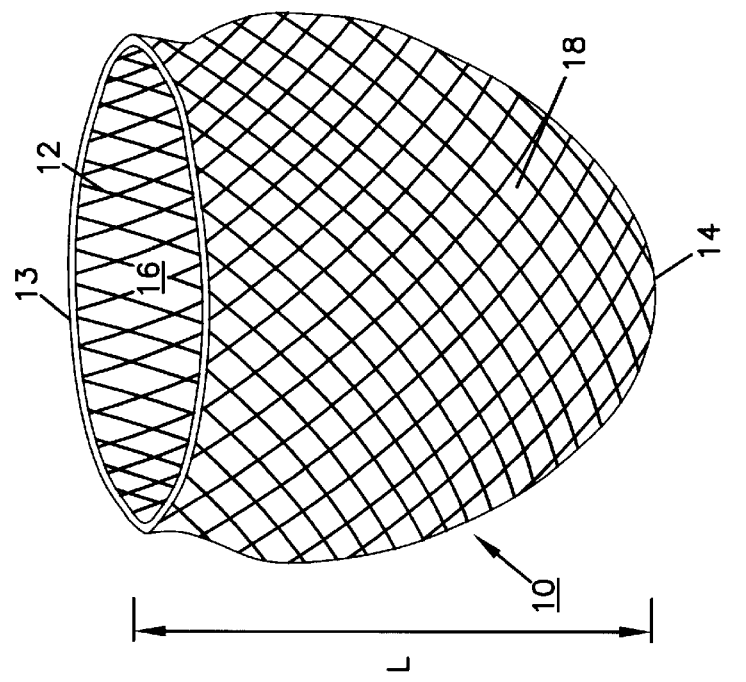
FIG. 3 is a perspective view of one embodiment of a cardiac constraint device.
Figure 4A:
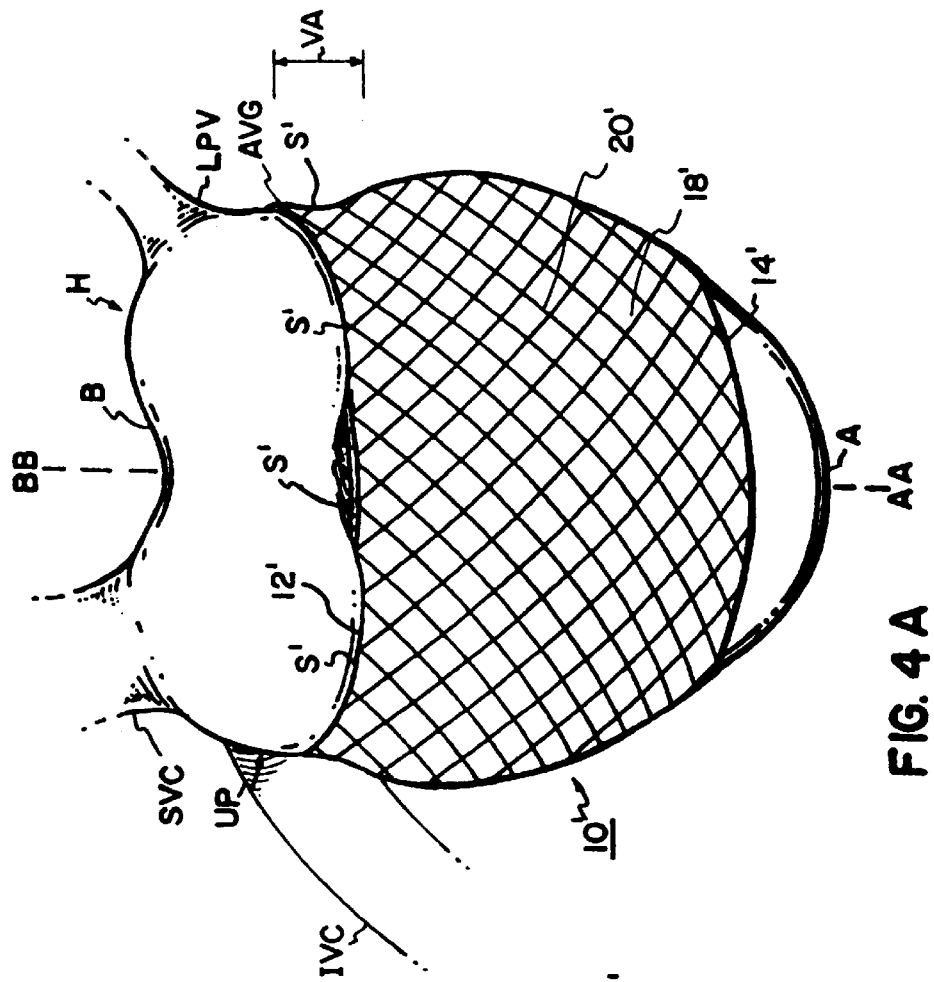
FIG. 4A is a side elevation view of a diseased heart in diastole with the device of FIG. 4 in place.
Figure 4:
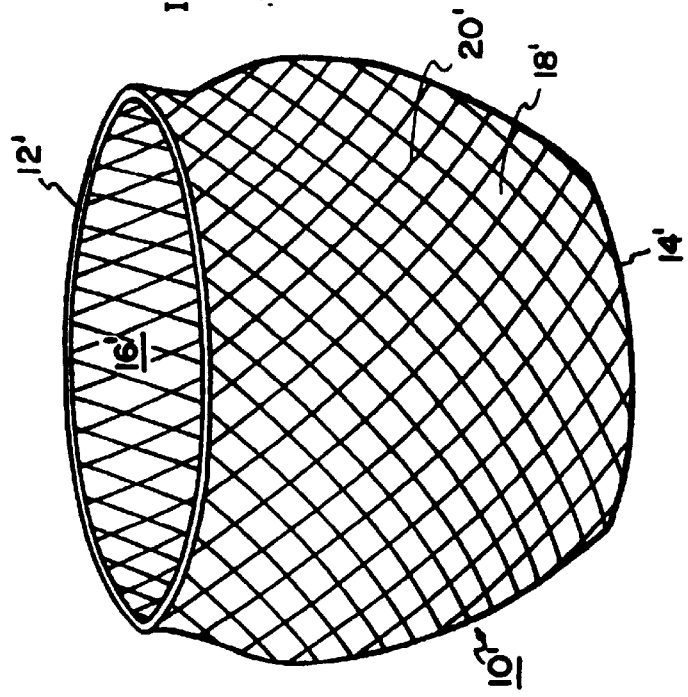
FIG. 4 is a perspective view of an alternative cardiac constraint device.

With reference now to FIGS. 3, 3A, 4 and 4A, the cardiac constraint device is shown as a jacket 10, 10' of flexible, biologically compatible material. The jacket 10, 10' is an enclosed knit material having upper and lower ends 12, 12', 14, 14'. The jacket 10, 10' defines an internal volume 16, 16' which is completely enclosed but for the open ends 12, 12' and 14'. In the embodiment of FIG. 3, lower end 14 is closed. In the embodiment of FIG. 4, lower end 14' is open. In both embodiments, upper ends 12, 12' are open. Throughout this description, the embodiment of FIG. 3 will be discussed. Elements in common between the embodiments of FIGS. 3 and 4 are numbered identically with the addition of an apostrophe to distinguish the second embodiment and such elements need not be separately discussed.

The jacket 10 is dimensioned with respect to a heart H to be treated. Specifically, the jacket 10 is sized for the heart H to be constrained within the volume 16. The jacket 10 can be slipped around the heart H. The jacket 10 has a length L between the upper and lower ends 12, 14 sufficient for the jacket 10 to constrain the lower portion LP. The upper end 12 of the jacket 10 extends at least to A-V groove AVG and further extends to the lower portion LP to constrain at least the lower ventricular extremities LE.

When the parietal pericardium is opened, the lower portion LP is free of obstructions for applying the jacket 10 over the apex A. If, however, the parietal pericardium is intact, the diaphragmatic attachment to the parietal pericardium inhibits application of the jacket over the apex A of the heart. In this situation, the jacket can be opened along a line extending from the upper end 12' to the lower end 14' of jacket 10'. The jacket can then be applied around the pericardial surface of the heart and the opposing edges of the opened line secured together after placed on the heart. Systems for securing the opposing edges are disclosed in, for example, U.S. Pat. No. 5,702,343, the entire disclosure of which is incorporated herein by reference. The lower end 14' can then be secured to the diaphragm or associated tissues using, for example, sutures, staples, etc.

In the embodiment of FIGS. 3 and 3A, the lower end 14 is closed and the length L is sized for the apex A of the heart H to be received within the lower end 14 when the upper end 12 is placed at the A-V groove AVG. In the embodiment of FIGS. 4 and 4A, the lower end 14' is open and the length L' is sized for the apex A of the heart H to protrude beyond the lower end 14' when the upper end 12' is placed at the A-V groove AVG. The length L' is sized so that the lower end 14' extends beyond the lower ventricular extremities LE such that in both of jackets 10, 10', the myocardium MYO surrounding the ventricles RV, LV is in direct opposition to material of the jacket 10, 10' during diastole. Such placement is desirable for the jacket 10, 10' to present a constraint against dilation of the ventricular portion of the heart H.

After the jacket 10 is positioned on the heart H as described above, the jacket 10 is secured to the heart. Preferably, the jacket 10 is secured to the heart H using sutures (or other fastening means such as staples). The jacket 10 is sutured to the heart H at suture locations S circumferentially spaced along the upper end 12. While a surgeon may elect to add additional suture locations to prevent shifting of the jacket 10 after placement, the number of such locations S is preferably limited so that the jacket 10 does not restrict contraction of the heart H during systole, While the jacket 10 is expandable due to its knit pattern, the fibers 20 of the knit fabric 18 are preferably non-expandable. While all materials expand to at least a small amount, the individual fibers 20 do not substantially stretch in response to force. In response to the low pressures in the heart H during diastole, the fibers 20 are generally inelastic. In a preferred embodiment, the fibers are 70 Denier polyester. While polyester is presently preferred, other suitable materials include polytetrafluoroethylene (PTFE), expanded PTFE (ePTFE) and polypropylene.

The knit material has numerous advantages. Such a material is flexible to permit unrestricted movement of the heart H (other than the desired constraint on circumferential expansion). The material is open defining a plurality of interstitial spaces for fluid permeability as well as minimizing the amount of surface area of direct contact between the heart H and the material of the jacket 10 (thereby minimizing areas of irritation or abrasion) to minimize fibrosis and scar tissue.

The open areas of the knit construction also allow for electrical connection between the heart and surrounding tissue for passage of electrical current to and from the heart.

For example, although the knit material is an electrical insulator, the open knit construction is sufficiently electrically permeable to permit the use of trans-chest defibrillation of the heart. Also, the open, flexible construction permits passage of electrical elements (e.g., pacer leads) through the jacket. Additionally, the open construction permits visibility of the epicardial surface, thereby minimizing limitations to performing other procedures, e.g., coronary bypass, to be performed without removal of the jacket.

The fabric 18 is preferably tear and run resistant. In the event of a material defect or inadvertent tear, such a defect or tear is restricted from propagation by reason of the knit construction.

The jacket 10 constrains further undesirable circumferential enlargement of the heart while not impeding other motion of the heart H. With the benefits of the present teachings, numerous modifications are possible. For example, the jacket 10 need not be directly applied to the epicardium (i.e., outer surface of the myocardium) but could be placed over the parietal pericardium. Further, an anti-fibrosis lining (such as a PTFE coating on the fibers of the knit) could be placed between the heart H and the jacket 10. Alternatively, the fibers 20 can be coated with PTFE.

The jacket 10 can be used in the early stages of congestive heart disease. For patients facing heart enlargement due to viral infection, the jacket 10 permits constraint of the heart H for a sufficient time to permit the viral infection to pass. In addition to preventing further heart enlargement, the jacket 10 treats valvular disorders by constraining circumferential enlargement of the valvular annulus and deformation of the ventricular walls.

C. Tensioning of the Jacket

Figure 5:
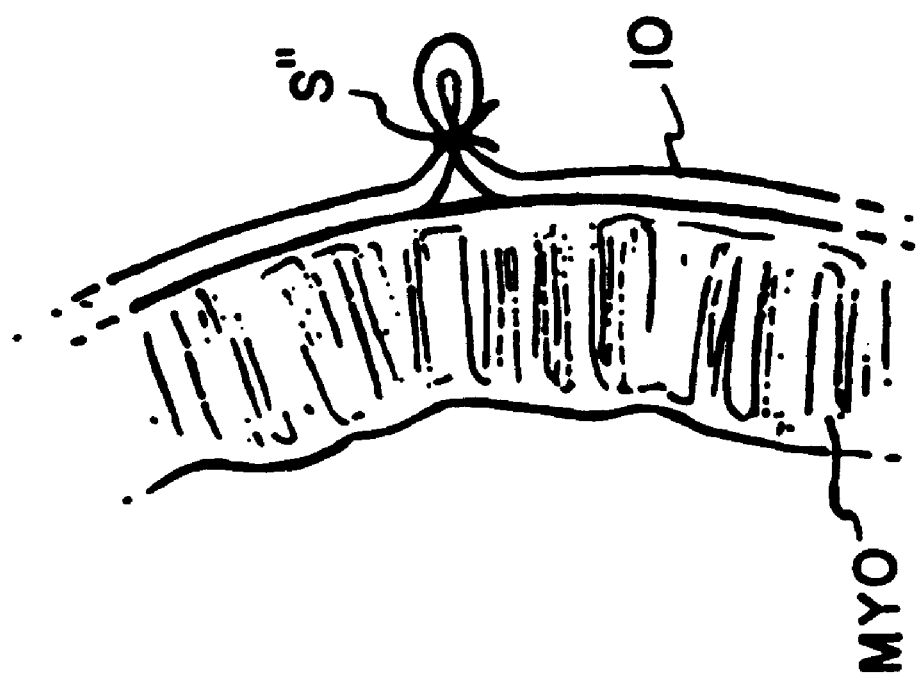
FIG. 5 is a cross-sectional view of the device of FIG. 3 overlying a myocardium and with the material of the device gathered for a snug fit.

To permit the jacket 10 to be easily placed on the heart H, the volume and shape of the jacket 10 are larger than the lower portion LP during diastole. So sized, the jacket 10 may be easily slipped around the heart H. Once placed, the jacket's volume and shape are adjusted for the jacket 10 to snugly conform to the external geometry of the heart H during diastole. Such sizing is easily accomplished due to the knit construction of the jacket 10. For example, excess material of the jacket 10 can be gathered and sutured S" (FIG. 5) to reduce the volume 16 of the jacket 10 and conform the jacket 10 to the shape of the heart H during diastole. Such shape represents a maximum adjusted volume.

According to the invention, the jacket 10 constrains enlargement of the heart H beyond the maximum adjusted volume without restricting contraction of the heart H during systole. As an alternative to gathering of FIG. 5, the jacket 10 can be provided with other arrangements for adjusting volume. For example, as disclosed in U.S. Pat. No. 5,702,343, the jacket can be provided with a slot. The edges of the slot can be drawn together to reduce the volume of the jacket.

The jacket 10 is adjusted to a snug fit on the heart H during diastole. Care is taken to avoid tightening the jacket 10 too much such that cardiac function is impaired. During diastole, the left ventricle LV fills with blood. If the jacket 10 is too tight, the left ventricle LV cannot adequately expand and left ventricular pressure will rise. During the fitting of the jacket 10, the surgeon can monitor left ventricular pressure. For example, a well-known technique for monitoring so-called pulmonary wedge pressure uses a catheter placed in the pulmonary artery. The wedge pressure provides an indication of filling pressure in the left atrium LA and left ventricle LV. While minor increases in pressure (e.g., 2–3 mm Hg) can be tolerated, the jacket 10 is snugly fit on the heart H but not so tight as to cause a significant increase in left ventricular pressure during diastole.

D. Heart Measurement

Jacket selection may be facilitated by a method for obtaining an accurate measurement of the heart's size prior to selecting a jacket 10. Co-pending U.S. application Ser. No. 09/399,703 (the "'703" application), now U.S. Pat. No. 6,179,791, discloses a device capable of measuring a heart. However, the configuration of the device of the '703 application requires invasive surgery to obtain the measurements. The present invention can obtain similar measurements using less invasive surgical techniques.

Two embodiments of the device are discussed below.

1. Hinged Measurement Device

Referring to FIG. 6, a device 30, for obtaining a measurement of a heart H is depicted. The device 30 includes a handle 31 having a distal end 32 and a proximal end 33. The device 30 also includes a measuring portion 24. In one embodiment, the proximal end 33 includes a hinged region 37. The handle 31 includes two handle members, a first handle member 35, and a second handle member 36. The first handle member 35 has a distal end 44 and a proximal end 46. The second handle member 36 has a distal end 45 and a proximal end 47.

The first and second handle members, 35 and 36, can be made of any material that is able to be sterilized. For all purposes throughout this disclosure, sterilization can be accomplished by any acceptable method, examples of which are: autoclaving (steam sterilization), dry-heat sterilization, gas sterilization (with ethylene oxide for example), radiation sterilization, filtration, sterilization by liquid sterilants, hydrogen peroxide vapor, hydrogen peroxide plasma, peroxy acetic acid, and UV radiation. For example, the first and second handle members, 35 and 36 can be made of a material typically used in the manufacturing of medical devices. Examples of suitable materials include plastics, such as polyethylene, annealed stainless steel, brass or aluminum.

The device 30 also includes a flexible member 40. The flexible member 40 contains at least one marked region. In one embodiment, the flexible member 40 includes a first non-marked region 41 and a second marked region 42. The second marked region 42 contains markings 43 evenly spaced apart by any convenient measurement unit (e.g. inches and fractions thereof, centimeters, millimeters, etc. . . . ). If desired, the flexible member 40 and first and second handle members 35 and 36 can be constructed using a disposable material that is cost effective to discard after every use.

Referring to FIG. 9, the flexible member 40 is further characterized. The flexible member 40 includes a proximal region 61, a transition region 60 and a distal region 62. The proximal region 61 is located within the first non-marked region 41 of the flexible member 40. The transition region 60 is also located within the first non-marked region 41 of the flexible member 40. The distal region 62 forms the remainder of the first non-marked region 41 and the second marked region 42 of the flexible member 40. The distal region 62 includes a distal end 63.

The proximal region 61 has a diameter or width greater than the diameter or width of the distal region 62. The difference in the diameter of the proximal region 61 and the distal region 62 is defined by the first handle member 35 as will be discussed below. Preferably the proximal region will have a diameter that is at least 20% larger than the distal region 62. The transition region 60 has a diameter that either gradually decreases from one end to the other, or decreases in a non-gradual manner. The decrease in diameter is defined by the difference in the diameter of the proximal region 61 and the distal region 62.

The flexible member 40 can be made of any material that can be sterilized, and is somewhat flexible. The flexible member 40 can be made of any material that can be sterilized, and is somewhat flexible, for example: a polymer with a durometer of 50 to 90 Shore A. Preferably, the flexible member 40 is made of a material typically used in the production of medical devices. Examples of material that could be used to make the flexible member 40 include plastics, such as polyethylene or PVC.

Referring to FIGS. 6 and 6a, the assembly of the device 30 using the above-discussed components will be discussed. The handle 31 comprises a first handle member 35 and a second handle member 36. The handle 31 may be configured so that the first and second handle members 35 and 36 are connected; for example through a hinge. If a hinge is utilized, it can be configured so that the first handle member 35 defines a connection receiving element 70. The second handle member 36 defines a connection element 38. The connection receiving element 70 and the connection element 38 can be configured in any way that allows connection between the first and second handle members 35 and 36. For example, the connection element 38 can be configured as an extension off of the second handle member 36 and the connection receiving element 70 can be an extension off the first handle member 35 that is configured for the connection element 38 to fit in. The handle 31 is assembled by connecting the first handle member 35 to the second handle member 36 by engaging the connection receiving element 70 of the first handle member 35 to the connection element 38 of the second handle member 36. The connection of the first and second handle members 35 and 36 defines a hinged region 37 at the proximal end 33 of the handle 31.

In one embodiment, the connection receiving element 70 of the first handle member 35 and the connection element 38 of the second handle member 36 are manufactured using the same material as the first and second handle members, 35 and 36. Typically the connection receiving element 70 and the connection element 38 are molded as part of the first and second handle members 35 and 36. Once the first handle member 35 is connected to the second handle member 36, a void 39 is created between the two handle members 35 and 36. The void 39 can be increased or decreased by separating the distal ends of the first and second handle members 35 and 36.

The first and second handle members 35 and 36 each define a lumen 71 and 72 respectively. The lumens 71 and 72 within the first and second handle members 35 and 36, respectively, run lengthwise, from the proximal to distal ends (or vice versa) of the first and second handle members 35 and 36.

Referring to FIGS. 7 and 8, one embodiment of a first handle member 35 is described. According to this embodiment, the distal end 44 of the first handle member 35 defines a first aperture 51. The first aperture 51 has a diameter 50 that is greater than the diameter of the distal region 62 of the flexible member 40, such that the distal region 62 of the flexible member 40 is able to freely move along the length of the lumen 71. The proximal end 46 of first handle member 35 defines a second aperture 53. The second aperture 53 has a diameter 52 that is greater than the diameter of the distal region 62, the transition region 60 and the proximal region 61 of flexible member 40, such that the distal region 62 of the flexible member 40 is able to freely move along the length of the lumen 71.

The lumen 71 of the first handle member 35 is defined by the first and second apertures 51 and 53, as discussed above. The lumen 71 of the first handle member 35 is further defined by the way in which the transition region 60 fits in it. The lumen 71 is configured so that the flexible member 40 cannot freely move through the entire length of the lumen 71 of the first handle member 35. The configuration of the lumen 71 is more fully described below in the section describing assembly of the device 30.

Referring to FIGS. 10 and 11, one embodiment of a second handle member 36 is described. According to this embodiment, the distal end 45 of a second handle member 36 defines a third aperture 55. The third aperture 55 has a diameter 54 greater than the diameter of the distal region 62 of the flexible member 40, such that the distal region 62 of the flexible member 40 can freely move through the lumen 72. The proximal end 47 of the second handle member 36 defines a fourth aperture 57. The fourth aperture 57 has a diameter 56 that is greater than the diameter of the distal region 62 of the flexible member 40, such that the distal region 62 can freely move through the lumen 72. In this embodiment, the lumen 72 of the second handle member 36 has a constant diameter along the length of the second handle member 36.

The device 30 is assembled by inserting the flexible member 40 inside the lumens 71, 72 of the handle members 35, 36. The procedure will now be explained with reference to FIGS. 6 through 9. First, the distal end 63 of the distal region 62 of the flexible member 40 is inserted into the second aperture 53 of the first handle member 35. The flexible member 40 is then threaded through the lumen 71 of the first handle member 35. Next, the distal end 63 of the distal region 62 of the flexible member 40 is threaded out of the lumen 71 of the first handle member 35 through the first aperture 51. The flexible member 40 is then threaded through the lumen 71 of the first handle member 35. The diameter of the lumen 71 of the first handle member 35 is configured such that the diameter of the lumen 71 at the proximal end 46 of the handle is greater than the diameter of the lumen 71 at the distal end 74 of the first handle member 35, such that the transition region 60 of the flexible member 40 cannot freely move along the entire length of the lumen 71 defined by the first handle member 35. The flexible member 40 is anchored in the lumen 71 of the first handle member 35 when the transition region 60 abuts the transition area 73 of the lumen 71.

Next, the distal end 63 of the distal region portion 62 of the flexible member 40 is threaded into the third aperture 55 of the second handle member 36 and threaded through the lumen 72 of the second handle member 36. The distal end 63 of the distal region 62 of the flexible member 40 is then threaded out of the fourth aperture 57 of the second handle member 36.

Once the device 30 is assembled, it has three parts, a handle 31, an adjustable loop 34, (made up of the flexible member 40) and a measurement region 49. The assembled device 30, can be used to measure different aspects of the heart.

One measurement that can be accomplished with the device 30 of the present invention is the size of the heart. The size of the heart can be measured using the device 30, as depicted in FIG. 12. First, the adjustable loop 34 is enlarged by increasing the length of the flexible member 40 extending between the handle members. The adjustable loop 34 is enlarged by urging the distal end 63 of the flexible member 40 towards the fourth aperture 57 of the second handle member 36, so that the flexible member 40 moves out of the third aperture 55 of the second handle member 36. The adjustable loop 34 can then be placed around the region of the heart H to be measured. The distal regions 44 and 45 of the handle members 35 and 36 are brought towards each other to minimize the void 39. Next, the distal end 63 of the flexible member 40 is pulled away from the fourth aperture 57 of the second handle member 36 such that excess flexible member 40 in the adjustable loop 34 is retracted back through the lumen 72 of the second handle member 36 until loop 34 fits snugly around the heart H.

One method of determining the value of this measurement of the heart is to note the specific marking 43 that is present at the intersection defined by the flexible member 40 and the fourth aperture 57 of second handle member 36.

The specific value for the measurement can also be determined in other ways and still be within the scope of the present invention. For example, the second handle member 36 could be equipped with a viewing window at its proximal end 47. The measurement would be given a value by noting the marking viewed through this window. Alternatively, the second handle member 36 could be configured to determine the value at the distal end 45. Generally, measurement is determined by comparing a first position on the flexible member 40 with a second position located somewhere on the second handle member 36. For example, the first position on the flexible member 40 could be where it extends out of the proximal end 47 of the second handle member 36, and the second position could be on the second handle member 36 where the flexible member 40 extends out of the second handle member 36.

In FIG. 13, the device 30 is being used to measure another aspect of the heart H, a surface length of the heart H. One such surface length of the heart H is from the A-V groove AVG to the apex A. If the device 30 being utilized has a hinge, the connection receiving element 70 of the first handle member 35 is disengaged from the connection element 38 of the second handle member 36. Then, the distal end 44 of first handle member 35 is placed against the heart H at the A-V groove AVG. The flexible member 40 is then placed along the heart H and the distal end 63 of the flexible member 40 is pulled away from the fourth aperture 57 of the second handle member 36 so that the portion of the flexible member 40 that made up the loop region 34 is decreased until the distal end 45 of the second handle member 36 is on the apex A of the heart H. The surface length of the heart can then be measured by comparing the first position on the flexible member 40 with the second position on the first handle member 35.

FIG. 14 depicts the device 30 measuring another measurement of the heart H; the apex A of the heart H. The device 30 is used in a manner analogous to that described above for measuring the surface length of the heart H from the A-V groove AVG to the apex A. It will be appreciated that any measurements of physical aspects of the heart can be undertaken with the device 30 of the invention.

FIG. 15 illustrates another embodiment of the invention. In this embodiment, the second handle member 36 is equipped with markings 70 evenly spaced apart by any convenient measurement unit (e.g. centimeters, inches or fractions thereof, millimeters, etc. . . . ) so that the second handle member 36 can also be used as a ruler. If desired, the first handle member 35 can be marked similarly. The first or second handle members 35 or 36 so marked can be used for other measurements of the heart H, such as to determine apex A to base B.

2. Non-Hinged Measurement Device

Another embodiment of the device of the invention is illustrated in FIGS. 16, 17, and 17a. The device 99 includes a first and second handle member 110 and 111 and a flexible member 101. FIG. 17A illustrates both a first and second handle member 110 and 111 and their corresponding elements. The first and second handle members 110 and 111 each define a lumen 120 and 121 along the length of the handle member 110, 111, respectively. The proximal end 106 and distal end 107 of the first handle member 110 define first and second apertures 122 and 123. The proximal end 108 and distal end 109 of the second handle member 111 define third and fourth apertures 124 and 125.

According to this embodiment, the diameter of the lumen 120 and 121 are constant along the length of the first and second handle members 110 and 111. In contrast to the first embodiment, the first handle member 110 does not have a lumen 120 configured to anchor the flexible member 101. Instead, the flexible member 101 is configured to be anchored within the lumen 120 of the first handle member 110. If desired, the handle members 110 and 111 can be identical and interchangeable.

As with the first embodiment, the first and second handle members 110 and 111, respectively, can be made of any material that is sterilizable. Preferably, the first and second handle members 110 and 111 are made of materials typically used in the manufacturing of medical devices. Examples of materials that could be used to make the first and second handle members 110 and 111 include plastics, such as polyethlyne, annealed stainless steel, brass or aluminum. If desired, the flexible member 101 and the first and second handle members 110 and 111 can be manufactured using a disposable material that is cost effective to discard after every use.

The flexible member 101 of device 99 again has a first non-marked region 103 and a second marked region 102 that includes markings 70 evenly spaced apart by any convenient measurement unit (e.g., inches, fractions thereof, centimeters or millimeters, etc. . . . ). The flexible member 101 includes an enlarged portion 104 on the proximal end 130 of the first non-marked region 103, and a distal end 131 of the second marked region 102. The enlarged portion 104 has a diameter that is greater than the diameter of all of the apertures 122, 123, 124 and 125 of the first and second handle members 110 and 111. In this embodiment, the distal end 131 has the same diameter as the remainder of the flexible member 101 (excluding the enlarged portion 104).

The flexible member 101 can be made of any material that can be sterilized, and is somewhat flexible, for example: a polymer with a durometer of 50 to 90 Shore A. Preferably, the flexible member 101 is made of a material typically used in the production of medical devices. Examples of material that could be used to make the flexible member 101 include plastics, such as polyethylene or PVC.

FIG. 18 depicts the assembled device 99. The distal end 131 of the flexible member 101 is threaded through the proximal end 106 of the first handle member 110. The flexible member 101 is then urged through the first lumen 120 of the first handle member 110 so it exits at the distal end 107 of the first handle member 110. The flexible member 101 is then urged through the lumen 120 of the first handle member 110 until the enlarged portion 104 abuts the proximal end 106 of the first handle member 110. The flexible member 101 is then threaded into the distal end 109 of the second handle member 111, extended through the lumen 121 of the second handle member 111, and extended out the proximal end 108 of the second handle member 111.

Thus, the device 99, has three parts: a two component handle 100, an adjustable loop 112, (made up of the flexible member 101) and a measurement region 113. This adjustable loop 112 along with the measurement region 113 are used to measure the heart.

FIG. 19 illustrates a close up view of the proximal end 132 of the device 99 showing one example of how a specific measurement can be read using the device 99. Once the adjustable loop 112 is fit snugly across or around the area of the heart H to be measured, the length of that region can be determined by noting the specific mark 120 at the intersection of the flexible member 101 and the proximal region 108 of the second handle member 111. This view also shows a close up of the interaction between the enlarged portion 104 of the flexible member 101 and the proximal region 106 of the first handle member 110 that anchors the flexible member 101 in the first handle member 110.

The specific value for the measurement can also be determined in other ways and still be within the scope of the present invention. For example, the first handle member 110 could be equipped with a viewing window at its proximal end 106. The measurement would be given a value by noting the marking viewed through this window. Alternatively, the first handle member 110 could be configured to determine the value at the distal end 107. Generally, measurement is determined by comparing a first position on the flexible member 101 with a second position located somewhere on the first handle member 110. For example, the first position on the flexible member 101 could be where it extends out of the proximal end 106 of the first handle member 110, and the second position could be on the first handle member 110 where the flexible member 101 extends out of the first handle member 110.

From the foregoing detailed description, the invention has been described in a preferred embodiment. Modifications and equivalents of the disclosed concepts are intended to be included within the scope of the appended claims.

What is claimed is:

1. A surgical tool for measuring physical characteristics of a heart, the tool comprising:
   a handle having first and second handle members, and a hinged region at a proximal end of said handle; and
   a flexible member,
   wherein said flexible member connects said first handle member and said second handle member at their distal ends, and wherein at least one of said handle members has a lumen.

2. The surgical tool of claim 1, wherein at least said second handle member has a lumen.

3. The surgical tool of claim 2, wherein said first and second handle members have lumens.

4. The surgical tool of claim 1, wherein said lumen of at least one said handle member runs lengthwise within said handle member.

5. The surgical tool of claim 4, wherein said lengthwise running lumen has a constant diameter throughout the length of said lumen.

6. The surgical tool of claim 4, wherein said lengthwise running lumen has a non-constant diameter throughout the length of said lumen.

7. The surgical tool of claim 6, wherein said non-constant diameter of said lumen has proximal and distal regions.

8. The surgical tool of claim 7, wherein said diameter at said proximal region is larger than said diameter at said distal region.

9. A surgical tool for measuring physical characteristics of a heart, the tool comprising:
   a handle having first and second handle members, and a hinged region at a proximal end of said handle; and
   an essentially cylindrical flexible member having a proximal end and a distal end with a variable diameter from said proximal to said distal end,
   wherein said flexible member connects said first handle member and said second handle member.

10. The surgical tool of claim 9, wherein said essentially cylindrical flexible member has a greater diameter at said proximal end than said distal end.

11. A surgical tool for measuring a heart, the tool comprising:
   a first and second handle member, wherein said handle members have proximal and distal ends, and include internal passageways that run lengthwise through from said proximal to said distal end of said handle members;
   a flexible member, wherein said flexible member is cylindrically shaped, has a proximal end that is non-marked and a distal end that is marked, and said proximal end is larger in diameter than said distal end;
   a hinged region, wherein said hinged region comprises a connection receiving portion on said first handle member and a connection portion on said second handle member, wherein said distal end of said flexible member passes through the internal passageway of said first handle member from the proximal end of said first handle member to the distal end of said first handle member, extends out, passes through the internal passageway of said second handle member from the distal end to the proximal end of said second handle member.

12. The surgical tool of claim 11, wherein said proximal end of said cylindrical flexible member is configured so that said flexible member is anchored in said first handle member.

13. The surgical tool of claim 11, wherein said first and said second handle members are different.

14. The surgical tool of claim 13, wherein said internal passageway of said first handle member is configured so that said flexible member is anchored in said first handle member.

* * * * *